US011071187B1

(12) United States Patent
Maa et al.

(10) Patent No.: US 11,071,187 B1
(45) Date of Patent: Jul. 20, 2021

(54) CIRCADIAN RHYTHMS ENTRAINMENT ENHANCEMENT DEVICE

(71) Applicant: Aleddra Inc., Renton, WA (US)

(72) Inventors: Chia-Yiu Maa, Bellevue, WA (US); Chun-Te Yu, Bellevue, WA (US)

(73) Assignee: Aleddra Inc., Renton, WA (US)

( * ) Notice: Subject to any disclaimer, the term of this patent is extended or adjusted under 35 U.S.C. 154(b) by 0 days.

(21) Appl. No.: 17/090,697

(22) Filed: Nov. 5, 2020

(51) Int. Cl.
*H05B 47/11* (2020.01)
*H05B 47/115* (2020.01)
(Continued)

(52) U.S. Cl.
CPC ........... *H05B 47/11* (2020.01); *A61N 5/0618* (2013.01); *H05B 45/10* (2020.01); *H05B 45/60* (2020.01);
(Continued)

(58) Field of Classification Search
CPC ...... H05B 45/20; H05B 47/16; H05B 47/105; H05B 47/19; H05B 45/10; H05B 45/24; H05B 45/22; H05B 47/11; H05B 47/115; H05B 3/008; H05B 45/28; H05B 45/325; H05B 47/10; H05B 45/30; H05B 47/12; H05B 47/155; H05B 47/18; H05B 45/3725; H05B 45/44; H05B 45/60; H05B 45/395; H05B 47/125; H05B 47/175; H05B 33/08; H05B 45/3578; H05B 45/36; H05B 45/375; H05B 45/38; H05B 45/385; H05B 45/46; F21V 29/74; F21V 29/70; F21V 23/006; F21V 15/01; F21V 19/006; F21V 19/02; F21V 21/02; F21V 21/30; F21V 23/003; F21V 23/0442; F21V 23/0464; F21V 23/0471; F21V 23/0478; F21V 23/06; F21V 9/08; F21V 14/02; F21V 21/005; F21V 33/006; F21V 7/04; F21V 1/00; F21V 23/00; F21V 13/04; F21V 15/015; F21V 7/0008; F21V 7/0025; F21V 7/0033; F21V 7/0083; H01S 5/0085; H01S 5/0087; H01S 5/0215; H01S 5/0217; H01S 5/02212; H01S 5/02251; H01S 5/02255; H01S 5/02325;
(Continued)

(56) References Cited

U.S. PATENT DOCUMENTS 9,854,640 B2 * 12/2017 Hsia .................. H05B 45/60
9,955,551 B2 * 4/2018 Spero .................. F21S 4/28
(Continued)

*Primary Examiner* — Monica C King
(74) *Attorney, Agent, or Firm* — Andy M. Han; Han IP PLLC

(57) ABSTRACT

A circadian entrainment enhancement device includes a housing, a first directional light source, a second directional light source, and a driver. During daytime, the driver turns on the first directional light source with a high melanopic ratio to enhance the daytime circadian entrainment of a user. During nighttime, the driver turns on the second directional light source with a low melanopic ratio to enhance the nighttime circadian entrainment of a user. A more advanced version of the present disclosure uses a light sensor, a memory module, and a computation module to calculate the necessary light output of the device by factoring the ambient light level into consideration. An even more advanced version of the present disclosure uses a distance sensor to adjust the light level of the light sources according to the distance between the device and the user.

28 Claims, 4 Drawing Sheets

(51) Int. Cl.
  *H05B 45/00* (2020.01)
  *A61N 5/06* (2006.01)
  *H05B 45/10* (2020.01)

(52) U.S. Cl.
  CPC .... *H05B 47/115* (2020.01); *A61N 2005/0653* (2013.01)

(58) Field of Classification Search
  CPC ............ H01S 5/02345; H01S 5/02375; H01S 5/02469; H01S 5/0287; H01S 5/22; H01S 5/34333; H01S 5/4012; H01S 5/4031; B60Q 1/04; B60Q 1/085; B60Q 1/1423; B60Q 2300/054; B60Q 2300/112; B60Q 2300/116; B60Q 2300/122; B60Q 2300/134; B60Q 2300/142; B60Q 2300/21; B60Q 2300/23; B60Q 2300/312; B60Q 2300/314; B60Q 2300/322; B60Q 2300/41; B60Q 2300/42; B60Q 3/18; B60Q 3/72; B60Q 3/80; B60Q 9/00
  See application file for complete search history.

(56) References Cited

U.S. PATENT DOCUMENTS 10,420,185 B2 * 9/2019 Biery ..................... H05B 47/19
10,609,798 B1 * 3/2020 Maa ....................... H05B 45/20

* cited by examiner

CIRCADIAN RHYTHMS ENTRAINMENT ENHANCEMENT DEVICE

BACKGROUND

Technical Field

The present disclosure pertains to the field of circadian devices and, more specifically, proposes a circadian entrainment enhancement device.

Description of Related Art

It is well known that circadian rhythm affects the behavior of animals, including human, and the circadian rhythm is entrained by the 24-hour light-dark cycle of sunlight. When the circadian rhythm is disrupted, there would be negative impact on the health of a person. Studies have shown that people now spend 90% of their time indoor under electrical light, are deprived of sunlight. If an environment is not well lit, thus not providing sufficient circadian stimulus, the biological alertness of an occupant in such environment may be impaired. Similarly, if an environment is over lit at night, the biological system of an occupant would remain in high alert and the occupant may have a difficulty to fall asleep. The sleep quality of this occupant may also be negatively affected.

The building and the light industries have recognized the need of having a proper circadian stimulus for the daytime and a different circadian stimulus the nighttime, in addition to the light level requirement, which is defined by footcandle. Several circadian stimulus metrics have been proposed, such as equivalent melanopic lux (EML), circadian stimulus (CS), melanopic to photopic ratio (M/P ratio), just to name a few. The International WELL Building Institute (IWBI) has published a set of circadian lighting design requirements for different environments based on the EML metric (https://standard.wellcertified.com/light/circadian-lighting-design). For example, the IWBI requirements state that for work areas, for all workstations, electric lights provide maintained illuminance on the vertical plane facing forward (to simulate the view of the occupant) of 150 EML or greater. The EML is defined as follows:

$$EML = L \times R,$$

where L is the visual lux and R is the M/P ratio of the light source.

It is worth mentioning that the EML metric used by IWBI focuses on visual lux on the vertical plane, i.e., the vertical lux as perceived by an occupant, which is different from the illuminance on the horizontal plane, the horizontal lux. Therefore, the follow-up discussion would focus on the vertical EML, which equals to the vertical lux multiplied by the M/P ratio of the light source.

When designing the lighting for a new building, a lighting designer has new fixtures at his/her disposal for meeting the IWBI circadian lighting design requirements. For an existing environment, there are lamps and fixtures in place already, and may even be energy-efficient lighting equipment. Yet, such environment may still fall short of meeting the vertical EML requirement as defined by IWBI. To replace them all with new fixtures may be too costly. It can be argued that a more effective approach would be to enhance the vertical EML where it is lacking, i.e., by enhancing the vertical EML as perceived by an occupant.

SUMMARY

The present disclosure introduces a circadian entrainment enhancement device that could be used by any occupant personally to meet the vertical EML requirements set by IWBI for daytime and nighttime, without going through a complete lighting retrofit for the environment of the occupant. The present disclosure is not meant to be used as the sole light source in an environment. Rather, it is meant to compensate the existing light source(s) in the environment and enhance the vertical EML perceived by an occupant to meet the IWBI lighting requirements, thus resulting in an circadian entrainment enhancement.

In one aspect, the present disclosure comprises a housing, a first directional light source, and a first driver. A directional light source is used, as opposed to an omnidirectional light source, since the intent is for the present disclosure to shine its light directionally to the eyes of a user. The housing houses the first directional light source and the first driver. The first driver is configured to drive the first directional light source to generate a fixed first light output. The first directional light source has a first melanopic ratio >0.80. A high melanopic ratio >0.80 is critical for ensuring the light source could provide adequate circadian stimulus to a user during daytime, therefore enhancing the circadian entrainment of the user. Color rendering index (CRI) or the color temperature of the first directional lighting is not directly correlated to the circadian entrainment, and thus are not used as a qualifying factor in selecting the first directional light source. Moreover, the first directional light source is configured to provide at least 50 equivalent melanopic lux (EML) at 60 cm at 0-degree lighting zone. The 0-degree lighting zone refers the light emitted out of a light source at 0-degree horizontally. The 50 EML is chosen as the minimal light output level for the first directional light source. This 50 EML falls below what is required by IWBI lighting requirements, which states >150 EML for work areas. This is because it is assumed that there exists a primary light source in an environment where the present disclosure is used, and the purpose of the present disclosure is meant to supplement to, rather than replace, the primary lighting source in the environment. When the primary light source provides a low EML to a user, it is foreseeable to use the present disclosure with its first directional light source having >50 EML at 60 cm at 0-degree lighting zone, e.g., 100 EML or even 150 EML. The 60 cm distance at 0-degree zonal light implies the present disclosure will be use in a close distance from the eyes of a user, for example, the present disclosure may be placed above a computer monitor or a laptop computer, and the light emitted out of the present disclosure shines directly into the eyes of the user. Lastly, the present disclosure is configured to shine a light of the first directional light source horizontally to the eyes of the user, thus providing an effective vertical lux to the eyes of the user.

In some embodiments, the first directional light source may have a spectral distributor (SPD) greater than 15% in a 440~490 nm wavelength range. The light in the 440~490 nm wavelength range has been shown to be directly correlated to the melatonin suppression. A higher SPD ratio in the 440~490 nm wavelength range guarantees a more effective circadian entrainment, whereas a lower SPD ration in this wavelength range would have a lesser effect on circadian entrainment.

In some embodiments, the first directional light source comprises one or more organic light emitting diodes (OLEDs). In some other embodiments, the first directional light source comprises one or more OLEDs. Both LED and OLED are good directional light source candidates.

In some embodiments, a vertical beam angle of the present disclosure is less than 30 degrees with respect to a horizontal plane. This is to emphasize that the present disclosure is designed to only shine directly and vertically into the eyes of a user and is not meant for general lighting applications.

In some embodiments, the present disclosure is disposed at least 30 cm from the eyes of the user. Therefore, the present disclosure may not be an eyewear device. For the present disclosure to provide at least 50 EML at 60 cm, it could provide almost 200 EML at 30 cm, since the spectral power is proportional to the inverse of the square of the distance. It would be too bright to use this present disclosure at a distance shortly than 30 cm from the eyes of an user.

In some embodiments, the present disclosure further comprises a second directional light source and a second driver. The first directional light source and the first driver are for enhancing the daytime circadian entrainment, whereas the second directional light source and the second driver are for enhancing the nighttime circadian entrainment. The second driver is configured to drive the second directional light source to generate a fixed second light output. In actual implementation, the first driver and the second driver may be implemented via one physical driver circuitry. The second directional light source has a second melanopic ratio <0.40, which is for ensuring the second directional light source would not suppress the melatonin of a user, thus not keeping the user on a high alert at night. Moreover, the second directional light source is configured to provide no more than 50 EML at 60 cm at 0-degree lighting zone. There is no minimum light output level for the second directional light source, but only the maximum light output level, to meet the IWBI lighting design requirement for nighttime. Lastly, the present disclosure is configured to shine a light of the second directional light source horizontally to the eyes of the user.

In some embodiments, the second directional light source has an SPD<3% in a 440~490 nm wavelength range. This requirement refines the constraint on the second directional light source to ensure it would not have sufficient SPD ratio to effectively suppress the melatonin of a user.

In some embodiments, the ratio of the SPD of the first directional light source in a 470~480 nm wavelength range to the SPD of the second directional light source in a 470~480 nm wavelength range is at least 10 to 1. This requirement highlights the proportional spectral power of the first and the second directional light sources in the most critical wavelength range, namely, 470~480 nm, as related to melatonin suppression. For example, an embodiment may have the SPD ratio of its first directional light source in the 470~480 nm wavelength range may be 10%, whereas the SPD ratio of its second directional light source in the 470~480 nm wavelength range may be 0.5% or even lower.

In some embodiments, the first directional light source and the second directional light source are configured such that only one of them is turned on at a time, but not simultaneously. Thus, the operation of the first directional light source and the second directional light source is mutually exclusive. In this scenario, since only one of the two light directional light sources will be on at a time, it is foreseeable that the first and the second driver may be implemented via one physical driver.

In some embodiments, the second directional light source comprises one or more OLEDs. In some other embodiments, the second directional light source comprises one or more OLEDs. Both LED and OLED are good directional light source candidates.

In some embodiments, the present disclosure further comprises a dimmer. Moreover, the first driver is a dimmable driver, and it is controllable via the dimmer to set the first light output of the first directional light source. Similarly, in some other embodiments, the present disclosure further comprises a dimmer. The second driver is a dimmable driver, and it is controllable via the dimmer to set the second light output of the second directional light source. In the scenario where the operation of the first directional light source and the second directional light source is mutually exclusively, it is foreseeable to use one dimmer for dimming the first dimmable driver when the first directional light source is on, and for dimming the second dimmable driver when the second directional light source is on.

In another aspect, the present disclosure comprises a housing, a first directional light source, and a first tunable driver, a first memory module, a first computational module, and a light sensor. The housing houses the first directional light source, the first tunable driver, the first memory module, the first computation module, and the light sensor. The first tunable driver is configured to drive the first directional light source to generate a variable first light output. The first directional light source has a first melanopic ratio $R_1>0.80$. The light sensor is configured to measure the vertical lux $L_A$ of the ambient light with respect to the device in accordance with the present disclosure. It is assumed that the vertical lux $L_A$ of the ambient light measured by the present disclosure approximates as the vertical lux $L_A$ observed by the user. The first memory module stores Illuminating Engineering Society (IES) data of the first directional light source and the configuration information used by the first computational module. The first computational module is configured to set the melanopic ratio Rai of the ambient light of the present disclosure and store the configuration information to the first memory module. For example, $R_A$ may be set to 0.5 in general or 0.8 for a well-lit environment. For more advanced embodiments, $R_A$ may vary from environment to environment, and may even varies from time to time. It may also vary due to the amount of daylight exposure. The first computational module is configured to set a first EML target to $EML_{T1}$. Note that $EML_{T1}$ may vary from environment to environment. In fact, IWBI standard defines different $EML_{T1}$ for different environment, e.g., 200 EML for work areas or 150 EML for living environments.

The first computation module is configured to take the first melanopic ratio $R_1$, the vertical lux $L_A$ of the ambient light, the melanopic ratio $R_{A1}$ of the ambient light, the first EML target $EML_{T1}$, and the IES data of the first directional light source for calculating the first target lux $L_{T1}$ of the first directional light source such that the combination of the EML from the ambient light and the EML of the first directional light source at 0-degree lighting zone approximates the first EML target $EML_{T1}$. The first computation module is further configured to adjust the first tunable driver for setting the light output of first directional light source to be the first target lux $L_{T1}$ at 0-degree lighting zone at zero distance. The statements above can be represented by the following formula:

$$EML_{T1}=L_A \times R_{A1}+L_{T1} \times R_1$$

In other words, the first EML target $EML_{T1}$ is achieved by the combination of the EML from the ambient light, $L_A \times R_A$, and the EML from the first directional light source. The first computational module can then determine the first EML target $EML_{T1}$ according to the following formula:

$$L_{T1}=(EML_{T1}-L_A \times R_{A1})/R_1$$

Once $L_{T1}$ is calculated, the first computational module can then reference the IES data of the first directional light source stored in the first memory module to determine the light output of the first directional light source in meeting the first target lux $L_{T1}$ at 0-degree lighting zone at zero distance, and then it can adjust the first tunable driver for setting the light output of first directional light source accordingly. When the ambient light already provides sufficient EML, i.e., $L_A \times R_A > EML_{T1}$, the first computational module will turn off the first directional light source. Lastly, the present disclosure is configured to shine a light of the first directional light source horizontally to the eyes of the user. The workflow for calculating lux $L_{T1}$ is summarized in FIG. 1, and the last step of the workflow is for the first computational module to look up the IES data in the first memory module in order to determine the necessary wattage of the first driver to deliver lux $L_{T1}$ at 0-degree lighting zone at zero distance.

The above calculation takes a simplified approach, since this is based on the assumption that the first target lux $L_{T1}$ at zero distance of the first directional light source may be the vertical lux observed by the eyes of a user at a distance >0. This simplified approach may be acceptable if the distance from the first directional light source to the eyes of the user is short, e.g., 2 cm. However, when the eyes of the user are 60 cm away from the first directional light source, it would be necessary to factor in this distance in order to ensure that the first directional light would generate sufficient light output such that it can deliver the first target lux $L_{T1}$ at 0-degree lighting zone at the distance 60 cm.

To factor in the distance between the present disclosure and the eyes of a user, in some embodiments, the present disclosure further comprises a distance sensor which is housed by the housing. The distance sensor is configured to measure the distance D between the present disclosure and the user. The first computation module is configured to take the first melanopic ratio $R_1$, the vertical lux $L_A$ of the ambient light, the melanopic ratio $R_{A1}$, of the ambient light, the first EML target $EML_{T1}$, the IES data of the first directional light source, and the distance D for calculating the first target lux $L_{T1}$ of the first directional light source such that the combination of the EML from the ambient light and the EML of the first light source at 0-degree lighting zone approximates the first EML target $EML_{T1}$. The first computation module is further configured to adjust the first tunable driver for setting the light output of the first directional light source to meet the first target lux $L_{T1}$ at 0-degree lighting zone at the distance D (e.g., 100 lux), by generating a much higher light output out of the directional light source light $L_{T1}$ at 0-degree lighting zone at the distance 0 (e.g. 150 lux). The workflow for calculating lux $L_{T1}$ is summarized in FIG. 2, with an additional step of getting the distance between the device and the user from the distance sensor, before the first computational module looking up the IES data in the first memory module in order to determine the necessary wattage of the first driver to deliver lux $L_{T1}$ at 0-degree lighting zone at the distance D.

In some embodiments, the vertical lux $L_A$ is configured by having the light source measuring the horizontal lux of the ambient light with respect to the device, where the horizontal lux is defined as the visual lux on the horizontal plane. Then the first computation module uses a conversion ratio to covert the horizontal lux to the vertical lux $L_A$.

In some embodiments, the first directional light source has a spectral power distribution (SPD)>15% in a 440~490 nm wavelength range.

In some embodiments, the first directional light source comprises one or more light emitting diodes (LEDs). In some other embodiments, the first directional light source comprises one or more organic light emitting diodes (OLEDs).

In some embodiments, a vertical beam angle of the present disclosure is less than 30 degrees with respect to a horizontal plane.

In some embodiments, the present disclosure further comprises a second directional light source, a second tunable driver, a second memory module, and a second computation module. The housing houses the second directional light source, the second tunable driver, the second memory module, and the second computational module. The second driver is configured to drive the second directional light source to generate a variable second light output. The second directional light source has a second melanopic ratio $R_2 < 0.40$. The second memory module stores the IES data of the second directional light source and the configuration information used by the second computational module.

The second computational module is configured to set the melanopic ratio $R_{A2}$ of the ambient light of the present disclosure and store the configuration information to the second memory module. The second computational module is configured to set a second EML target $EML_{T2}$. $EML_{T2}$ may vary from environment to environment. IWBI standard defines different $EML_{T1}$ for different environment, e.g., 50 EML for living environments at night. The second computation module is configured to take the second melanopic ratio $R_2$, the vertical lux $L_A$ of the ambient light, the melanopic ratio $R_{A2}$, of the ambient light, the second EML target $EML_{T2}$, and the IES data of the second directional light source for calculating the second target lux $L_{T2}$ of the second directional light source such that the combination of the EML from the ambient light and the EML of the second directional light source at 0-degree lighting zone approximates the second EML target $EML_{T2}$. The second computation module is further configured to adjust the second tunable driver for setting the light output of second directional light source to be the second target lux $L_{T2}$ at 0-degree lighting zone at zero distance. The statements above can be represented by the following formula:

$$EML_{T2} = L_A \times R_{A2} + L_{T2} \times R_2$$

In other words, the second EML target $EML_{T2}$ is achieved by the combination of the EML from the ambient light, $L_A \times R_A$, and the EML from the second directional light source. The second computational module can then determine the second EML target $EML_{T2}$ according to the following formula:

$$L_{T2} = (EML_{T2} - L_A \times R_{A2})/R_2$$

Once $L_{T2}$ is calculated, the second computational module can then reference the IES data of the second directional light source stored in the second memory module to determine the light output of the second directional light source in meeting the second target lux $L_{T2}$ at 0-degree lighting zone at zero distance, and then it can adjust the second tunable driver for setting the light output of second directional light source accordingly. When the ambient light already provides sufficient EML, i.e., $L_A \times R_A > EML_{T2}$, the second computational module will turn off the second directional light source. Lastly, the present disclosure is configured to shine a light of the second directional light source horizontally to the eyes of the user.

The differentiation between the first and the second memory modules is logical, not physical. The first memory module stores the information related to the first directional light source whereas the second memory module stores the information related to the second directional light source. In actual implementation, one physical memory module may be used to store the information of both the first and the second directional light sources. Similarly, the differentiation between the first and the second computational modules is logical, not physical. The first computation module performs necessary calculation related to the first directional light source whereas the second computational module performs necessary calculation related to the second directional light source. In actual implementation, one physical computational processing unit may be able to perform all calculation related to both the first and the second computational modules.

In some embodiments, the housing further houses a distance sensor. The distance sensor is configured to measure the distance D between the device and the user. The second computation module is configured to take the second melanopic ratio $R_2$, the vertical lux $L_A$ of the ambient light, the melanopic ratio $R_{A2}$, of the ambient light, the second EML target $EML_{T2}$, the IES data of the second directional light source, and the distance D for calculating the second target lux $L_{T2}$ of the second directional light source such that the combination of the EML from the ambient light and the EML of the second light source at 0-degree lighting zone approximates the second EML target $EML_{T2}$. The second computation module is further configured to adjust the second tunable driver for setting the light output of second directional light source to meet the second target lux $L_{T2}$ at 0-degree lighting zone at the distance D.

In some embodiments, the second directional light source has an SPD<3% in a 440~490 nm wavelength range.

In some embodiments, the ratio of the SPD of the first directional light source in a 470~480 nm wavelength range to the SPD of the second directional light source in a 470~480 nm wavelength range is at least 10 to 1.

In some embodiments, the first directional light source and the second directional light source are configured such that only one of them is turned on at a time, but not simultaneously. Since only one of the two light directional light sources will be on at a time, the first and the second tunable drivers may be implemented via one physical driver.

In some embodiments, the second directional light source comprises one or more LEDs. In some other embodiments, the second directional light source comprises one or more OLEDs.

DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of circadian entrainment enhancement device having different form factors.

Example Implementations

Figure 3:
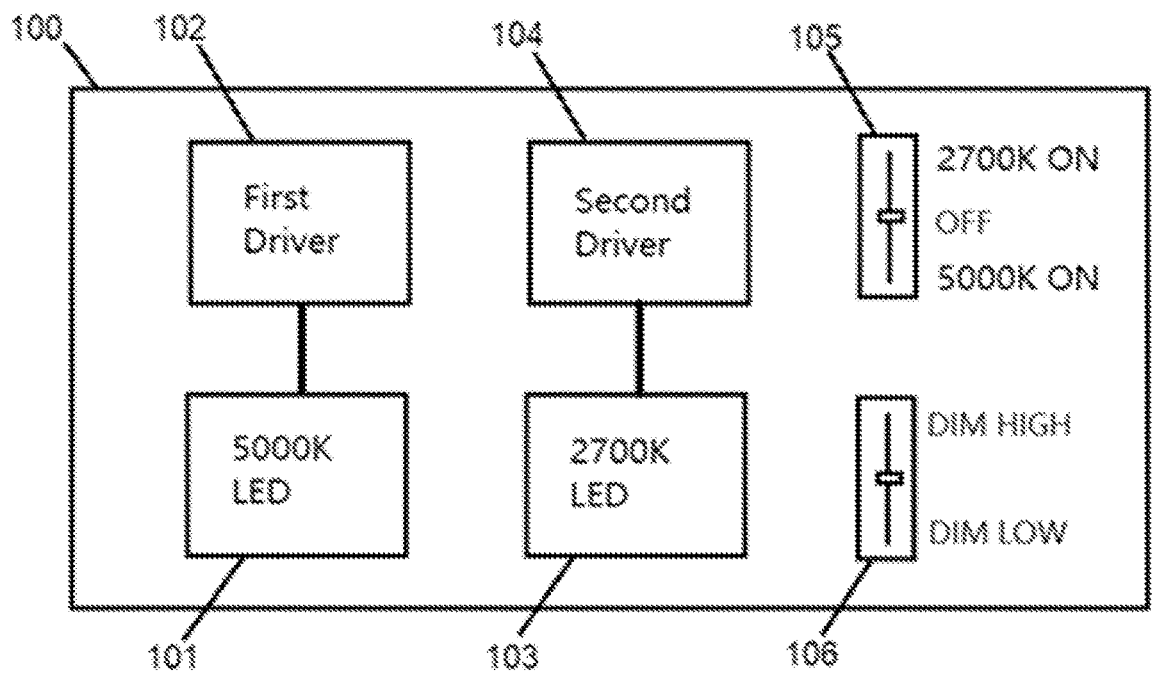
FIG. 3 schematically depicts an embodiment of the present disclosure.

The FIG. 3 schematically depicts an embodiment 100 of the present disclosure. The first directional light source 101 comprises 5000K LED's with a melanopic ratio >0.80, and it provides at least 50 equivalent melanopic lux (EML) at 60 cm at 0-degree lighting zone. Moreover, the first directional light source 101 has a spectral power distribution (SPD) >15% in a 440~490 nm wavelength range. The second directional light source 103 comprises 2700K LED's with a melanopic ratio <0.40, and it provides at most 50 EML at 60 cm at 0-degree lighting zone. Moreover, the second directional light source 103 has an SPD<3% in a 440~490 nm wavelength range. Additionally, the ratio of the SPD of the first directional light source 101 in a 470~480 nm wavelength range to the SPD of the second directional light source 103 in a 470~480 nm wavelength range is over 10 to 1. A selection switch 105 is used to turn on either the first directional light source 101 or the second directional light source 103. When the first directional light source 101 is on, the dimmer 106 controls the dimmable first driver 102 to generate out of the first directional light source 101 a first light output in a range of 50 to 200 EML at 60 cm at 0-degree lighting zone. When the second directional light source 103 is on, the dimmer 106 controls the dimmable second driver 104 to generate out of the second directional light source 103 a second light output in a range of 0 to 50 EML at 60 cm at 0-degree lighting zone.

Figure 4:
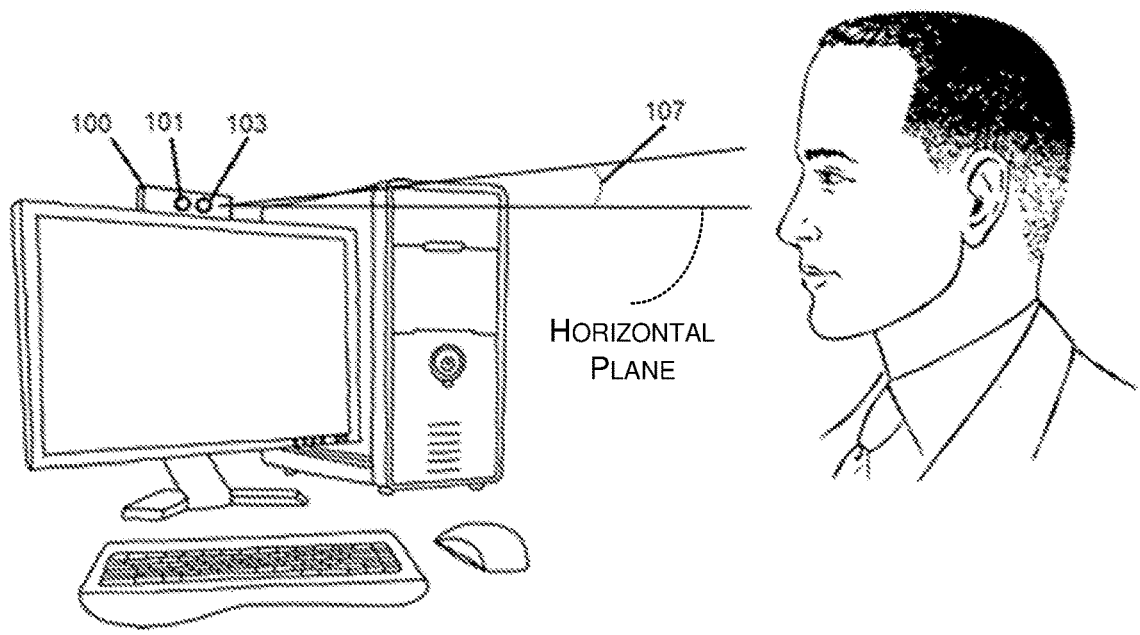
FIG. 4 schematically depicts how the device is positioned when in use relative to the position of a user.

As shown in FIG. 4, the embodiment 100 is configured to shine a light of the first directional light source 101 and the second directional light source 103 horizontally to the eyes of a user by being placed on top of a computer screen. The distance of the device is at least 30 cm from the eyes of the user. Moreover, the vertical beam angle 107 of the embodiment 100 is less than 30 degrees with respect to a horizontal plane, as shown in FIG. 4. The first directional light source 101 and the second directional light source 103 can be easily implemented by OLED light sources.

Figure 5:
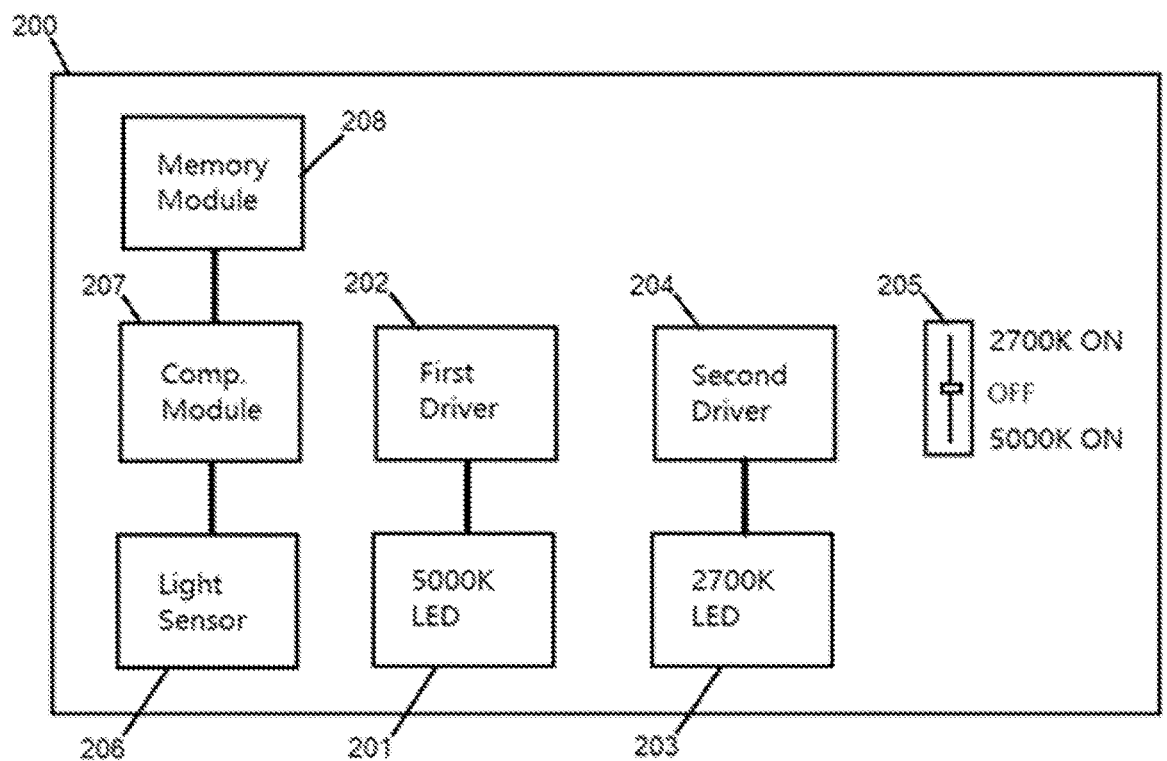
FIG. 5 schematically depicts another embodiment of the present disclosure with a light sensor.

The FIG. 5 schematically depicts another embodiment 200 of the present disclosure. The first directional light source 201 comprises 5000K LED's with a melanopic ratio >0.80. Moreover, the first directional light source 201 has an SPD>15% in a 440~490 nm wavelength range. The second directional light source 203 comprises 2700K LED's with a melanopic ratio <0.40. Moreover, the second directional light source 203 has an SPD<3% in a 440~490 nm wavelength range. Additionally, the ratio of the SPD of the first directional light source 201 in a 470~480 nm wavelength range to the SPD of the second directional light source 203 in a 470~480 nm wavelength range is over 10 to 1. The memory module 208 stores the IES data of the first directional light source 201, the IES data of the second directional light source 203, the melanopic ratio $R_{A1}$ and the target $EML_{T1}$ (for $L_{T1}$ calculation), and the melanopic ratio $R_{A2}$ and the target $EML_{T2}$ (for $L_{T2}$ calculation).

Figure 1:
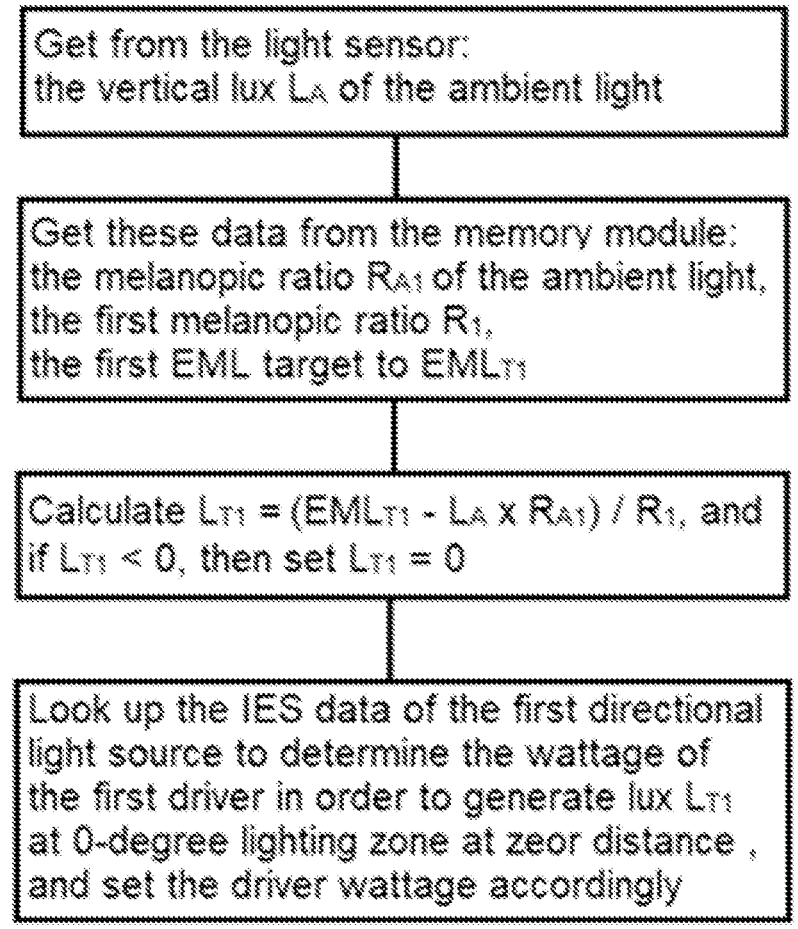
FIG. 1 shows the workflow of calculating the first target lux $L_{T1}$ and determining the first driver wattage.

A selection switch 205 is used to turn on either the first directional light source 201 or the second directional light source 203. When the first directional light source 201 is on, the computational module 207 calculates $L_{T1}$ according to the workflow shown in FIG. 1. Once is $L_{T1}$ is calculated, the computational module looks up the IES data of the first directional light source 201 to set the wattage output of the first driver 202 such that the first directional light source 201 would produce $L_{T1}$ at 0-degree lighting zone at zero distance. Similarly, when the second directional light source 203 is on, the computational module 207 calculates $L_{T2}$ according to the workflow similar to the one shown in FIG. 1 (by replacing $L_{T1}$, $EML_{T1}$, $R_{A1}$, $R_1$ with $L_{T2}$, $EML_{T2}$, $R_{A2}$, $R_2$, respectively). Once is $L_{T2}$ is calculated, the computational module looks up the IES data of the second directional light source 203 to set the wattage output of the second driver 204 such that the second directional light source 203 would produce $L_{T2}$ at 0-degree lighting zone at zero distance.

Similar to the embodiment 100 as shown in FIG. 4, the embodiment 200 is configured to shine a light of the first directional light source 201 and the second directional light source 203 horizontally to the eyes of a user by being placed on top of a computer screen. Moreover, the vertical beam angle of the embodiment 200 is less than 30 degrees with respect to the horizontal plane. The first directional light source 201 and the second directional light source 203 can be easily implemented by OLED light sources.

Figure 6:
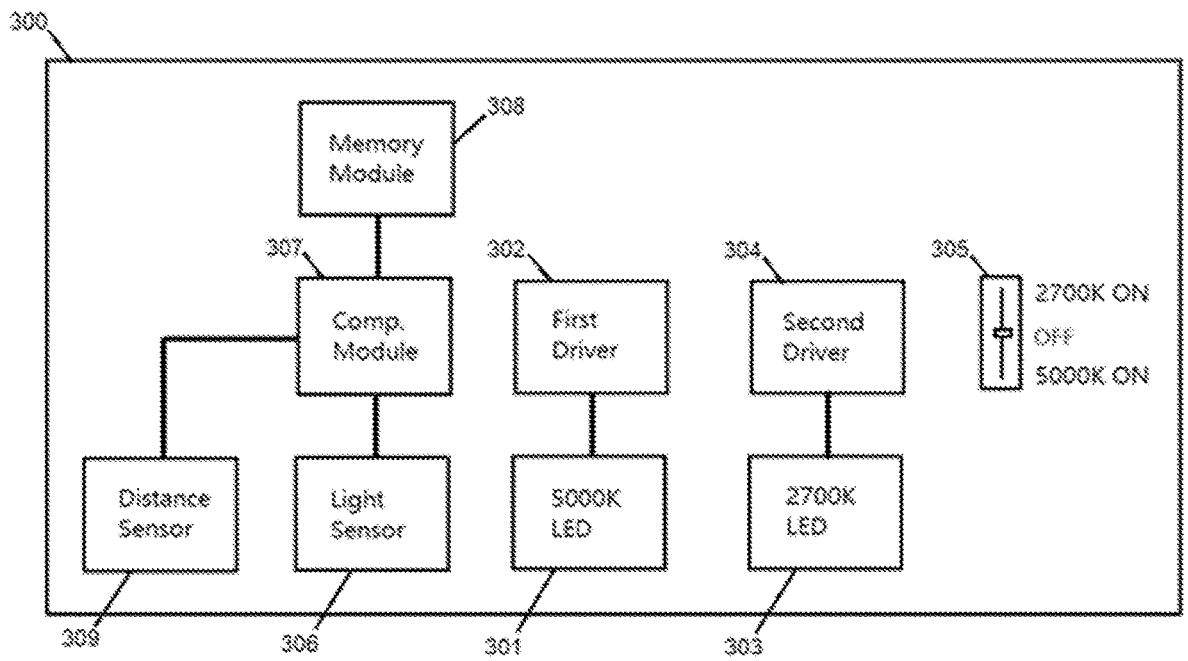
FIG. 6 schematically depicts yet another an embodiment of the present disclosure with a distance sensor.

The FIG. 6 schematically depicts yet another embodiment 300 of the present disclosure. The first directional light source 301 comprises 5000K LED's with a melanopic ratio >0.80. Moreover, the first directional light source 301 has an SPD>15% in a 440~490 nm wavelength range. The second directional light source 303 comprises 2700K LED's with a melanopic ratio <0.40. Moreover, the second directional light source 303 has an SPD<3% in a 440~490 nm wavelength range. Additionally, the ratio of the SPD of the first directional light source 301 in a 470~480 nm wavelength range to the SPD of the second directional light source 303 in a 470~480 nm wavelength range is over 10 to 1. The memory module 308 stores the IES data of the first directional light source 301, the IES data of the second directional light source 303, the melanopic ratio $R_{A1}$ and the target $EML_{T1}$ (for $L_{T1}$ calculation), and the melanopic ratio $R_{A2}$ and the target $EML_{T2}$ (for $L_{T2}$ calculation).

Figure 2:
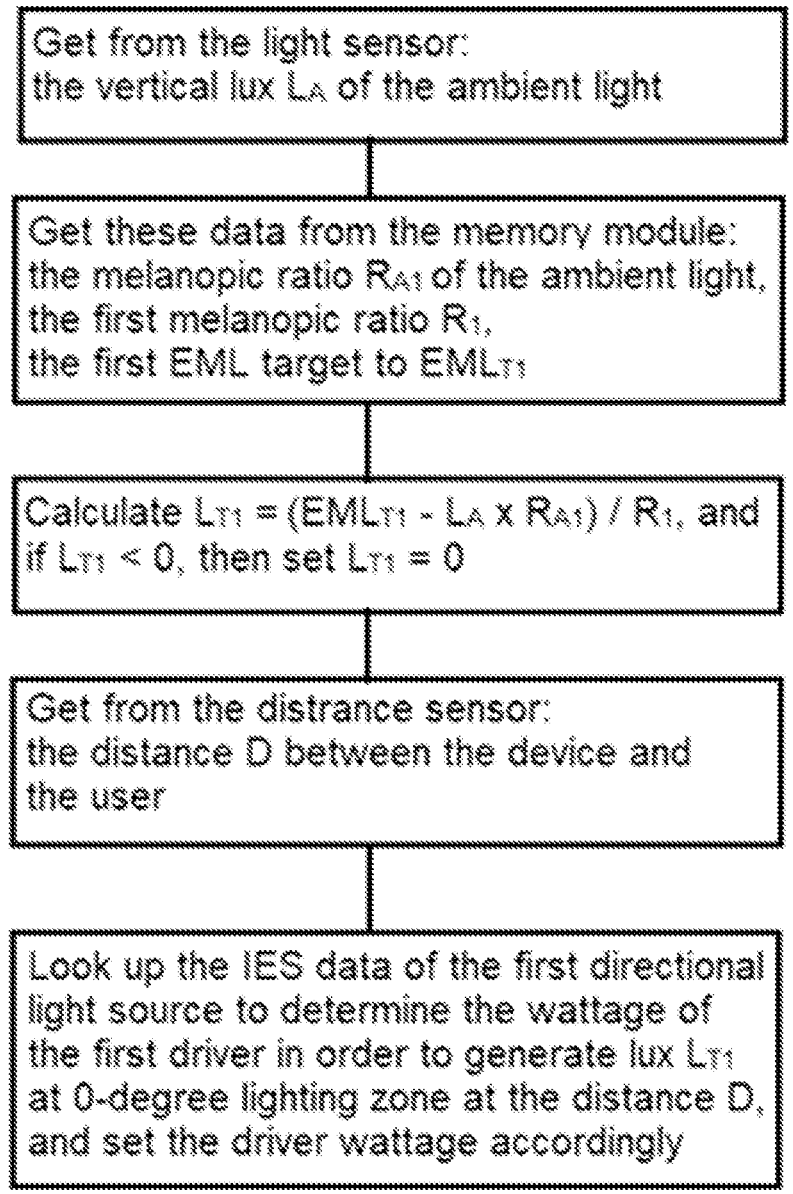
FIG. 2 shows the workflow of calculating the first target lux $L_{T1}$ and determining the first driver wattage with the consideration of the distance between the device and the user.

A selection switch 305 is used to turn on either the first directional light source 301 or the second directional light source 303. When the first directional light source 301 is on, the computational module 407 calculates $L_{T1}$ according to the workflow shown in FIG. 2. Once is $L_{T1}$ is calculated, the computational module looks up the IES data of the first directional light source 301 to set the wattage output of the first driver 302 such that the first directional light source 301 would produce $L_{T1}$ at 0-degree lighting zone at distance D, where D is the distance between the device and the user and is provided by the distance sensor 309. Similarly, when the second directional light source 303 is on, the computational module 307 calculates $L_{T2}$ according to the workflow similar to the one shown in FIG. 2 (by replacing $L_{T1}$, $EML_{T1}$, $R_{A1}$, $R_1$ with $L_{T2}$, $EML_{T2}$, $R_{A2}$, $R_2$, respectively). Once is $L_{T2}$ is calculated, the computational module would look up the IES data of the second directional light source 303 to set the wattage output of the second driver 304 such that the second directional light source 303 would produce $L_{T2}$ at 0-degree lighting zone at distance D.

Similar to the embodiment 100 as shown in FIG. 4, the embodiment 300 is configured to shine a light of the first directional light source 301 and the second directional light source 303 horizontally to the eyes of a user by being placed on top of a computer screen. Moreover, the vertical beam angle of the embodiment 300 is less than 30 degrees. The first directional light source 301 and the second directional light source 303 can be easily implemented by OLED light sources.

ADDITIONAL AND ALTERNATIVE IMPLEMENTATION NOTES

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A circadian entrainment enhancement device, comprising
   a housing;
   a first directional light source; and
   a first driver,
   wherein:
      the housing houses the first directional light source and the first driver,
      the first driver is configured to drive the first directional light source to generate a fixed first light output,
      the first directional light source has a first melanopic ratio >0.80,
      the first directional light source is configured to provide at least 50 equivalent melanopic lux (EML) at 60 cm at a 0-degree lighting zone, and
      the device is configured to shine a light of the first directional light source horizontally to eyes of a user.

2. The device of claim 1, wherein the first directional light source has a spectral power distribution (SPD)>15% in a 440~490 nm wavelength range.

3. The device of claim 1, wherein the first directional light source comprises one or more light emitting diodes (LEDs).

4. The device of claim 1, wherein the first directional light source comprises one or more organic light emitting diodes (OLEDs).

5. The device of claim 1, wherein a vertical beam angle of the device is less than 30 degrees with respect to a horizontal plane.

6. The device of claim 1, wherein the device is disposed at least 30 cm from the eyes of the user.

7. The device of claim 1, further comprising:
a second directional light source; and
a second driver,
wherein:
the housing further houses the second directional light source and the second driver,
the second driver is configured to drive the second directional light source to generate a fixed second light output,
the second directional light source has a second melanopic ratio <0.40,
the second directional light source is configured to provide no more than 50 EML at 60 cm at the 0-degree lighting zone, and
the device is configured to shine a light of the second directional light source horizontally to the eyes of the user.

8. The device of claim 7, wherein the second directional light source has a spectral power distribution (SPD)<3% in a 440~490 nm wavelength range.

9. The device of claim 7, wherein a ratio of the SPD of the first directional light source in a 470~480 nm wavelength range to the SPD of the second directional light source in the 470~480 nm wavelength range is at least 10 to 1.

10. The device of claim 7, wherein the first directional light source and the second directional light source are configured such that either of the first directional light source and the second directional light source is turned on at a time, but not simultaneously.

11. The device of claim 7, wherein the second directional light source comprises one or more light emitting diodes (LEDs).

12. The device of claim 7, wherein the second directional light source comprises one or more organic light emitting diodes (OLEDs).

13. The device of claim 1, further comprising:
a dimmer,
wherein the first driver is a dimmable driver controllable via the dimmer to set the first light output of the first directional light source.

14. The device of claim 7, further comprising:
a dimmer,
wherein the second driver is a dimmable driver controllable via the dimmer to set the second light output of the second directional light source.

15. A circadian entrainment enhancement device, comprising
a housing;
a first directional light source;
a first tunable driver;
a first memory module;
a first computational module;
a light sensor;
wherein:
the housing houses the first directional light source, the first tunable driver, the first memory module, the first computation module, and the light sensor;
the first tunable driver is configured to drive the first directional light source to generate a variable first light output,
the first directional light source has a first melanopic ratio $R_1 > 0.80$,
the light sensor is configured to measure a vertical lux $L_A$ of an ambient light with respect to the device,
the first memory module is configured to store Illuminating Engineering Society (IES) data of the first directional light source and configuration information used by the first computational module,
the first computational module is configured to set a melanopic ratio $R_{A1}$ of the ambient light of the device,
the first computational module is configured to set a first equivalent melanopic lux (EML) target to $EML_{T1}$,
the first computation module is configured to calculate a first target lux $L_{T1}$ of the first directional light source using the first melanopic ratio $R_1$, the vertical lux $L_A$ of the ambient light, the melanopic ratio $R_{A1}$ of the ambient light, the first EML target $EML_{T1}$, and the IES data of the first directional light source such that a combination of an EML from the ambient light and an EML of the first directional light source at a 0-degree lighting zone approximates the first EML target $EML_{T1}$,
the first computation module is further configured to adjust the first tunable driver to set the light output of first directional light source to be the first target lux $L_{T1}$ at the 0-degree lighting zone at zero distance, and
the device is configured to shine a light of the first directional light source horizontally to eyes of the user.

16. The device of claim 15, further comprising:
a distance sensor,
wherein:
the housing further houses the distance sensor,
the distance sensor is configured to measure a distance D between the device and the user,
the first computation module is configured to calculate the first target lux $L_{T1}$ of the first directional light source using the first melanopic ratio $R_1$, the vertical lux $L_A$ of the ambient light, the melanopic ratio $R_{A1}$, of the ambient light, the first EML target $EML_{T1}$, the IES data of the first directional light source, and the distance D such that a combination of the EML from the ambient light and an EML of the first light source at the 0-degree lighting zone approximates the first EML target $EML_{T1}$, and
the first computation module is further configured to adjust the first tunable driver to set the light output of the first directional light source to meet the first target lux $L_{T1}$ at the 0-degree lighting zone at the distance D.

17. The device of claim 15, wherein the vertical lux $L_A$ is configured by the light source measuring a horizontal lux of the ambient light with respect to the device and the first computation module to convert the horizontal lux to the vertical lux $L_A$ using a conversion ratio.

18. The device of claim 15, wherein the first directional light source has a spectral power distribution (SPD)>15% in a 440~490 nm wavelength range.

19. The device of claim 15, wherein the first directional light source comprises one or more light emitting diodes (LEDs).

20. The device of claim 15, wherein the first directional light source comprises one or more organic light emitting diodes (OLEDs).

21. The device of claim 15, wherein a vertical beam angle of the device is less than 30 degrees with respect to a horizontal plane.

22. The device of claim 15, further comprising:
a second directional light source;
a second tunable driver;
a second memory module; and
a second computational module,
wherein:
   the housing further houses the second directional light source, the second tunable driver, the second memory module, and the second computational module,
   the second driver is configured to drive the second directional light source to generate a variable second light output,
   the second directional light source has a second melanopic ratio $R_2<0.40$,
   the second memory module stores IES data of the second directional light source and configuration information used by the second computational module,
   the second computational module is configured to set a melanopic ratio $R_{A2}$ of the ambient light of the device,
   the second computational module is configured to set a second EML target to $EML_{T2}$,
   the second computation module is configured to calculate the second target lux $L_{T2}$ of the second directional light source using the second melanopic ratio $R_2$, the vertical lux $L_A$ of the ambient light, the melanopic ratio $R_{A2}$, of the ambient light, the second EML target $EML_{T2}$, and the IES data of the second directional light source a such that a combination of the EML from the ambient light and an EML of the second directional light source at the 0-degree lighting zone approximates the second EML target $EML_{T2}$,
   the second computation module is further configured to adjust the second tunable driver to set the light output of second directional light source to be the second target lux $L_{T2}$ at the 0-degree lighting zone at zero distance, and
   the device is configured to shine a light of the second directional light source horizontally to the eyes of the user.

23. The device of claim 22, further comprising:
a distance sensor,
wherein:
   the housing further houses the distance sensor,
   the distance sensor is configured to measure a distance D between the device and the user,
   the second computation module is configured to calculate the second target lux $L_{T2}$ of the second directional light source using the second melanopic ratio $R_2$, the vertical lux LA of the ambient light, the melanopic ratio $R_{A2}$, of the ambient light, the second EML target $EML_{T2}$, the IES data of the second directional light source, and the distance D such that a combination of the EML from the ambient light and an EML of the second light source at the 0-degree lighting zone approximates the second EML target $EML_{T2}$, and
   the second computation module is further configured to adjust the second tunable driver to set the light output of second directional light source to meet the second target lux $L_{T2}$ at the 0-degree lighting zone at the distance D.

24. The device of claim 22, wherein the second directional light source has an SPD<3% in a 440~490 nm wavelength range.

25. The device of claim 22, wherein a ratio of the SPD of the first directional light source in a 470~480 nm wavelength range to the SPD of the second directional light source in the 470~480 nm wavelength range is at least 10 to 1.

26. The device of claim 22, wherein the first directional light source and the second directional light source are configured such that either of the first directional light source and the second directional light source is turned on at a time, but not simultaneously.

27. The device of claim 22, wherein the second directional light source comprises one or more light emitting diodes (LEDs).

28. The device of claim 22, wherein the second directional light source comprises one or more organic light emitting diodes (OLEDs).

* * * * *